(12) United States Patent
Ikemoto et al.

(10) Patent No.: US 6,497,898 B1
(45) Date of Patent: *Dec. 24, 2002

(54) SURFACTANT, AND AN EMULSION-TYPE COSMETIC COMPOSITION AND A LIPSOME CONTAINING SAID SURFACTANT

(75) Inventors: Takeshi Ikemoto, Kanagawa (JP); Hiromi Minamino, Kanagawa (JP); Yasushi Sumida, Kanagawa (JP); Yoh-ichi Inoue, Kanagawa (JP)

(73) Assignee: Kanebo LTD, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/628,674
(22) PCT Filed: May 31, 1994
(86) PCT No.: PCT/JP94/00874
§ 371 (c)(1), (2), (4) Date: May 13, 1996
(87) PCT Pub. No.: WO95/09692
PCT Pub. Date: Apr. 13, 1995

(30) Foreign Application Priority Data

Oct. 7, 1993 (JP) .............................. 5-277653

(51) Int. Cl.$^7$ ............... A61K 9/127; A61K 9/00; A61K 6/00
(52) U.S. Cl. ............... 424/450; 424/400; 424/401
(58) Field of Search ............... 424/450, 401, 424/400, 70.1, 70.13; 252/108

(56) References Cited

U.S. PATENT DOCUMENTS

| | | | |
|---|---|---|---|
| 2,893,990 A | | 7/1959 | Hass et al. |
| 3,867,301 A | * | 2/1975 | Watanabe et al. ............ 252/108 |
| 3,963,699 A | | 6/1976 | Rizzi et al. |
| 5,268,180 A | | 12/1993 | Morancais et al. ......... 424/450 |

FOREIGN PATENT DOCUMENTS

| | | |
|---|---|---|
| JP | 59-106423/1984 | 6/1984 |
| JP | 60-258195/1985 | 12/1985 |
| JP | 61-207324/1986 | 9/1986 |
| JP | 61-289038/1986 | 12/1986 |
| JP | 62-500102/1987 | 1/1987 |
| JP | 64-075421 | 3/1989 |
| JP | 02 078 623 A | 3/1990 |
| JP | 3-157349/1991 | 7/1991 |
| JP | 4-300820/1992 | 10/1992 |
| JP | 05168893 * | 2/1993 |
| JP | 5-137994 | 6/1993 |
| JP | 5-168893 | 7/1993 |
| JP | 62-91236/1987 | 10/1994 |
| JP | 6-16688 | 1/2000 |
| JP | 52-6375/1977 | 1/2000 |
| JP | 53-6130/1978 | 1/2000 |
| JP | 36-21717/1961 | 1/2000 |
| JP | 59-16534/1984 | 1/2000 |
| JP | 56-55306/1981 | 2/2000 |
| WO | 86/03938 | 1/2000 |

OTHER PUBLICATIONS

R. Toubiana et al., "Synthése d'analogues du cord–factor: Partie II.—Préparation de 6,6'–dipalmitate de tréhalose par transestérification", Biochimie, 1973, vol. 55, 575–578.

J.H. Fuhrhop et al., Routes to Functional Vesicle Membranes Without Proteins, *Angewandte Chemie International Edition*, (Speyer, Germany) vol. 23, No. 2, Feb. 1984, pp. 100–113; p. 101, col. 2, para. 1, fig. 2.

Kunitake et al., *J. Am. Chem. Soc.*, vol. 99(11), p 3860, 1977.

K. Yoshimoto et al., Chemical and Biochemical Studies on Carbohydrate Esters: Synthesis of 6–0–, 6,6'–i–0–, and 4,6,4',6'–Tetra–0–stearoyl–α,α–trehaloses, *Chem. Pharm. Bull.* vol. 30(4). pp. 1169–1174 (1982).

Y. Nishikawa et al., Chemical and Biochemical Studies on Carbohydrate Esters: Anti Ehrlich Ascites Tumor Effect and chromatographic Behaviors of Fatty Acyl Monoesters of Sucrose and Trehalose *Chem. Pharm. Bull.*, vol. 25(7), pp 1717–1724 (1977).

T. Karingome, "Special Functional Surfactant," Oct. 31, 1988, CML p. 32–34.

* cited by examiner

*Primary Examiner*—Jose' G. Dees
*Assistant Examiner*—S. Gollamudi
(74) *Attorney, Agent, or Firm*—Pitney, Hardin, Kipp & Szuch, LLP

(57) ABSTRACT

The invention provides a surfactant comprising at least one trehalose-6-fatty acid ester selected from those represented by the following formula:

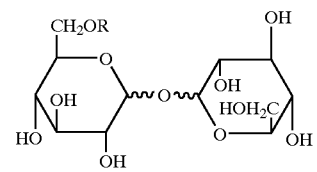

wherein R represents a saturated or unsaturated acyl group having 8–22 carbon atoms, and may have a hydroxyl group or other substituents, and an emulsion-type cosmetic composition comprising said surfactant and a water-soluble polymer. The surfactant of the invention has excellent surface activity and safety. Also, the emulsion-type cosmetic composition has excellent long-term storage stability and sensory properties, has no irritation to skin, and gives beautiful appearance with fine surface texture. Further, the invention is a liposome having a membrane wall composed of trehalose fatty acid ester. Said liposome has excellent chemical and physical stabilities such as long-term storage stability.

4 Claims, No Drawings

SURFACTANT, AND AN EMULSION-TYPE COSMETIC COMPOSITION AND A LIPSOME CONTAINING SAID SURFACTANT

FIELD OF THE INVENTION

The present invention relates to a surfactant which has excellent surface activity and safety.

The invention also relates to a detergent with excellent safety, containing the surfactant.

The invention further relates to an emulsion-type cosmetic composition with excellent emulsion stability, safety to skin and sensory properties, containing the surfactant.

BACKGROUND OF THE INVENTION

A number of compounds are known as surfactants and used in many applications. However, most of those surfactants irritate skin when they are used in cosmetics, such as shampoos, rinses, soaps and other cosmetic compositions, which contact with a human body directly. Therefore, lower irritating surfactants have been desired.

In many emulsions use is made of nonionic surfactants having a polyoxyethylene chain, anionic surfactants such as fatty acid soaps, cationic surfactants or ampholytic surfactants. However, there was a problem that emulsion-type cosmetic compositions with those synthetic surfactants generally tend to irritate skin. Also, even with nonionic surfactants which are said to be less irritating, most of them fit poorly to skin because of their polyoxyethylene chains.

On the other hand, alkylesterified sugars are nonionic surfactants which have been used widely in foods, cosmetics and the like. Among others, sucrose alkylesters in which sucrose constitutes a sugar skeleton are used widely and seen in many publications( Japanese Patent Application Laid Open No. 56-55306/1981). However,those are insufficient in sensory properties and long-term storage stability. Also, it is known to use, as a surfactant, trehalose-6,6'-dialkylester in which a trehalose derivative constitutes a sugar skeleton (Japanese Patent Application Laid Open Nos. 60-258195/1985 and 62-91236/1987). Those are insufficient in emulsifiability.

Synthesis of trehalose fatty acid ester are reported in Chem. Phar. Bull., 30 (4) pp 1169–1174, (1982), where synthesis of 6-stearoyl-trehalose and 6,6'-distearoyl-trehalose and the analysis of them using NMR, etc. are described. Those esters are reported to have anti-tumor activity against Ehrlich ascites tumor in mice. There is no description or suggestion that they show properties as a surfactant. An emulsion-type anti-tumor agent is known in which a specific emulsifier composition is combined with trehalose-6,6'-difatty acid ester as an anti-tumor agent in order to solve a disadvantage that the ester is difficult to dissolve in water (Japanese Patent Application Laid Open No. 61-289038/1986).

In consideration of surface activity, formability, washing ability and so forth for a surfactant, the presence of a single lipophilic moiety is said to be preferred. For example, glucose fatty acid monoester is reported in Japanese Patent Application Laid Open No. 03-157349/1991. However, this has a disadvantage that a stable emulsion can not be obtained due to its weak hydrophilicity.

DISCLOSURE OF THE INVENTION

A purpose of the invention is to provide a surfactant that has excellent surface activity and safety.

Another purpose of the invention is to provide a detergent that has excellent safety.

A further purpose of the invention is to provide an emulsion-type cosmetic that has low irritation to skin, long-term storage stability, excellent sensory properties and beautiful appearance with fine surface texture.

The present invention is a surfactant containing one or more of trehalose-6-fatty acid esters represented by the following formula:

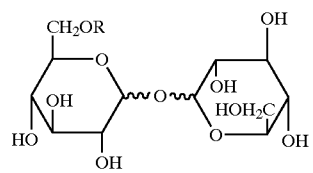

wherein R represents a saturated or unsaturated acyl group having 8–22 carbon atoms, and may have substituents such as a hydroxyl group.

One preferred embodiment of the invention is a surfactant containing 6-(10-undecylenyl)-trehalose represented by the following formula:

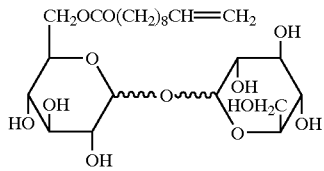

Another preferred embodiment of the invention is a surfactant containing 6-lauroyl-trehalose.

Further, another preferred embodiment of the invention is a surfactant containing 6-stearoyl-trehalose.

Also, the invention is a detergent characterized in that it contains a surfactant containing one or more of trehalose-6-fatty acid esters represented by the following formula:

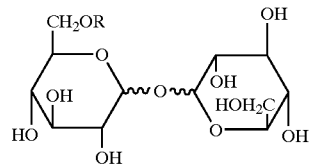

wherein R is a saturated or unsaturated acyl group having 8–22 carbon atoms, and may have substituents such as a hydroxyl group.

Further, the invention is an emulsion-type cosmetic composition characterized in that it contains one or more of trehalose-6-fatty acid esters represented by the following formula:

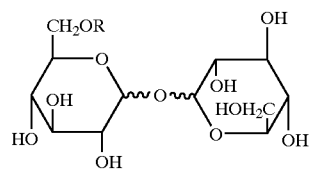

wherein R is a saturated or unsaturated acyl group having 8–22 carbon atoms, and may have substituents such as a hydroxyl; and a water-soluble polymer.

BEST MODE OF THE INVENTION

The trehalose-6-fatty acid ester of the invention can be obtained by a condensation reaction of trehalose with a fatty acid or by an ester interchange reaction between trehalose and a fatty acid ester.

Examples of the fatty acid or fatty acid ester which can be used in the invention include synthetic fatty acids and esters thereof, natural fatty acids, such as soybean fatty acid, beef tallow, cotton seed oil, olive oil, palm oil and so forth, and fatty acid esters thereof with lower alkyl groups, which esters are obtained in any conventional method.

Trehalose which can be used in the invention may be α,α-trehalose, α,β-trehalose, β,β-trehalose or mixtures thereof.

The trehalose-6-fatty acid of the invention can be obtained in any usual method of producing sucrose alkyl esters, as described in U.S. Pat. Nos. 2,893,990 and 3,963,699, Japanese Patent Application Laid Openlaid Nos. 36-21717/1961 and 53-6130/1978, all of which are incorporated herein by reference.

The trehalose-6-fatty acid ester is obtained as a main reaction product in these methods. In some cases, there are contained small amounts of unreacted trehalose and trehalose-6,6'-fatty acid diester as a side-reaction product. The trehalose-6-fatty acid ester may be purified in a conventional manner before used, if desired. However, the trehalose-6-fatty acid may be used together with small amounts of unreacted trehalose and trehalose-6,6'-fatty acid diester, because the trehalose-6-fatty acid can exhibit surface activity even in the presence of them.

The trehalose-6-fatty acid ester used in the invention is preferably those in which a fatty acid radical, i.e. an acyl group, has a linear or branched, saturated alkyl or alkenyl group having 8–22 carbon atoms. Examples of those include trehalose monocaprylate, trehalose mononanoate, trehalose monocaprate, trehalose monoundecanoate, trehalose monolaurate, trehalose monomyristate, trehalose monopalmitate, trehalose monostearate, trehalose monoarachidate, trehalose monobehenate, trehalose monoundecylenate, trehalose monooleate, trehalose monolinoleate, trehalose monolinolenate, trehalose monoisostearate, trehalose monohydroxystearate, and trehalose monoricinoleate. One or more from these trehalose-6-fatty acid esters can be used in the invention.

The surfactant of the invention preferably contains one or more selected from 6-(10-undecylenyl)-trehalose, 6-lauroyl-trehalose and 6-stearoyl-trehalose.

The surfactant of the invention has excellent surface activity and safety to skin and also may be used as an emulsifier in foods.

The skin or hair washing agent detergent of the invention preferably contains one or more of the trehalose-6-fatty acid ester in an amount of 1–50 wt. %, particularly 10–35 wt. %. It may further contain other surfactants.

The cosmetic composition of the invention contains one or more of the above trehalose-6-fatty acid ester and a water-soluble polymer. The content of the above trehalose-6-fatty acid ester in the cosmetic composition is preferably 0.01–20 wt. %, particularly 0.1–10 wt. %, based on the total weight of the cosmetic composition. If the content is less than 0.01 wt. %, the emulsion stability of the cosmetic composition tends to decrease during its storage. On the other hand, if it is more than 20 wt. %, it is difficult to obtain fine feeling in use.

The water-soluble polymer used in the invention may be generally any of those used in cosmetic compositions or pharmaceutical bases. Examples of the water-soluble polymer include guar gum, roastbean gum, queensseed, carageenan, galactan, arabic gum, tragacanth, pectin, mannan, starch, xanthan gum, dextrin, succinoglucan, curdlan, gelatin, casein, albumin, collagen, methyl cellulose, ethyl cellulose, hydroxyethyl cellulose, hydroxypropyl cellulose, carboxymethyl cellulose, methylhydroxypropyl cellulose, soluble starch, carboxymethyl starch, methyl starch, propyleneglycol alginate, salts of alginic acid, polyvinylalcohol, polyvinylpyrrolidone, polyvinylmethylether, carboxyvinyl polymers, sodium polyacrylate, polyethyleneglycol, ethylene oxide/propylene oxide copolymers, cationized cellulose, sodium chondroitin sulfate, and sodium hyaluronate. These water-soluble polymers may be used alone or in combination.

The content of the above water-soluble polymer is preferably 0.001–40 wt. %, particularly 0,01–20 wt. %, on the basis of the total weight of the cosmetic composition. If the content is less than 0.001 wt. %, the emulsion stability of the cosmetic composition tends to decrease during its storage. On the other hand, if it is more than 40 wt. %, it is difficult to obtain fine feeling in use.

The cosmetic composition of the invention may contain one or more oil substances that can usually be used in cosmetic compositions or pharmaceutical bases, if necessary, such as hydrocarbons, such as liquid paraffin, squalane, vaseline and microcrystalline wax; ester oils, such as isopropylmyristate, cetyl-2-ethylhexalate, glyceryl-tri-2-ethylhexanoate, vitamin C palmitate, vitamin C stearate, vitamin C sulfate and vitamin E acetate; waxes, such as beeswax and spermaceti; vegetable oils, such as avocado oil, almond oil, rice bran oil, olive oil, castor oil, rapeseed oil, saffron oil, corn oil, wheat germ oil, soybean oil, cotton-seed oil, tea-seed oil and jojoba oil; animal oils, such as turtle oil, mink oil and yolk oil; higher alcohols, such as cetyl alcohol, stearyl alcohol, oleyl alcohol, octyldodecanol and behenyl alcohol; higher fatty acids, such as laurylic acid, myristic acid, palmitic acid, stearic acid, oleic acid, linolic acid, linolenic acid, ricinoleic acid and isostearic acid; silicone oils, such as dimethylsilicone, methylphenylsilicone and cyclic silicone; other silicone resins and silicone polymers.

The cosmetic composition of the invention may contain polyvalent alcohols, such as ethyleneglycol, propyleneglycol, 1,3-butyleneglycol, dipropyleneglycol, glycerin, and polyglycerins such as diglycerin, triglycerin, tetraglycerin, pentaglycerin and hexaglycerin; trimethylolpropane, 1,2,6-hexatriol, glucose, maltose, maltitol, sucrose, fructose, xylitol, mannitol, sorbitol, maltotriose, threitol, sorbitan, starch-decomposed sugar and starch decompoed reducing alcohol, alone or in combination thereof.

The cosmetic composition of the invention may contain any ingredients customarily used in cosmetics and pharmaceutical bases, such as humectants, active ingredients, fragrances, preservatives, colorants, UV absorbents, astringents, synthetic surfactants, pigments(e.g., kaolin, mica, sericite, talc, yellow iron oxide, red iron oxide and titanium oxide) and water.

The cosmetic composition of the invention includes massage creams, cleansing creams, skin creams, foundation creams, makeup bases, hair creams, massage jellys, and medicinal jellys, but is not limited to those.

The invention will be explained further in detail in reference to the following Examples, but shall not be limited to those.

Preparation of Trehalose-6-fatty Acid Ester

EXAMPLE 1

Preparation of 6-(10-undecylenyl)-trehalose a) One hundred grams of α,α-trehalose were dissolved in 400 ml of dimethylformamide, to which added were 52.4 g of methyl 10-undecylenate and 1.0 g of potassium hydroxide, heated to 100° C. and then stirred for 12 hours. After this reaction solution was cooled, unreacted methyl 10-undecylenate was removed by extracting the solution with 400 ml of hexane three times. The dimethylformamide solution containing the desired substance was concentrated to about 200 ml in vacuum, to which, then, 1,000 ml of acetone was added to precipitate unreacted trehalose which was subsequently filtered out. The precipitate were washed with 100 ml of n-butanol, and the washing liquid was combined with the above filtrate. The filtrate was distilled in vacuum to obtain a yellowish viscous syrup. This viscous syrup was subjected to silica gel chromatography (developing solvent: chloroform/methanol=4/1) so as to remove remaining unreacted substances. A fraction containing the desired substance was distilled in vacuum to obtain 24.3 g of a yellowish viscous syrup.

b) The resultant syrup was analyzed by $^{13}$C-NMR spectroscopy. Signals were confirmed for a carbonyl group at 175.5 ppm, terminal methylene group at 140.11 and 114.73 ppm, and 6- and 6'-positions of trehalose at 64.4 and 62.64 ppm. This indicates the formation of 6-(10-undecylenyl)-trehalose.

EXAMPLE 2

Preparation of 6-lauroyl-trehalose

The procedures of Example 1a) were repeated with the exception that 62.5 g of methyl laurate was used instead of 52.4 g of methyl 10-undecylenate. 27.3 g of a white solid were obtained.

The resultant white solid was analyzed by $^{13}$C-NMR spectroscopy. Signals were confirmed for a carbonyl group at 175.5 ppm, and 6- and 6'-positions of trehalose at 64.4 and 62.64 ppm. The solid was analyzed by FAB-MS spectrometry with NaI and a peak at 547(M(molecular weight of the parent peak)+23) was confirmed. These indicate the formation of 6-lauroyl-trehalose.

EXAMPLE 3

Preparation of 6-stearoyl-trehalose

The procedures of Example 1a) were repeated with the exception that 87.1 g of methyl stearate was used instead of 52.4 g of methyl 10-undecylenate. 32.1 g of a white solid was obtained. The resultant white solid was analyzed by FAB-MS spectrometry with NaI and a peak at 631(M (molecular weight of the parent peak)+23) was confirmed. This indicates the formation of 6-stearoyl-trehalose.

EXAMPLE 4

Preparation of Trehalose-6-soybean Fatty Acid Ester

One hundred grams of α,α-trehalose were dissolved in 400 ml of dimethylformamide. To this solution added were 60 g of a methyester of soybean fatty acid and 1.0 g of potassium hydroxide, heated to 100° C., and then stirred for 18 hours. After this reaction solution was cooled, the unreacted methylester of soybean fatty acid was removed by extracting the reaction solution with 400 ml of hexane five times. The dimethylformamide solution containing the desired substance was concentrated to about 200 ml in vacuum, to which 1,500 ml of acetone was added to precipitate unreacted trehalose which was subsequently filtered off. The precipitates were washed with 100 ml of n-butanol, and the washing liquid was combined with the above filtrate. The filtrate was distilled in vacuum to obtain 41.6 g of trehalose-6-soybean fatty acid ester as a yellowish viscous syrup, which contained 6-linoleyl-trehalose as a primary component.

EXAMPLE 5

Preparation of Trehalose-6-palm Oil Fatty Acid Ester

The procedures of Example 4 were repeated with the exception that 60 g of a methylester of palm oil fatty acid were used instead of 60 g of methylester of soybean fatty acid to obtain 34.9 g of trehalose-6-palm oil fatty acid ester as a yellowish viscous syrup, which contained 6-lauroyl-trehalose as a primary component.

Safety Test

As a safety test on the above trehalose-6-fatty acid esters, irritation to skin was examinaed in accordance with the following procedures.

An adhesive plaster for patch test which had been impregnated with 1 ml of a 0.2% solution of the surfactant was put on 20 subjects for 24 hours. Irritaion was evaluated 24 hours after removing the patch. The result was rated by percentage of positive subjects who showed an clear erythema. The results are as shown in Table 1. Sodium laurylphosphate used as a control is a surfactant which is usually used in shampoos, body shampoos and the like.

TABLE 1

| Sample (0.1% solution) | Irritation to skin, positive, % |
| --- | --- |
| 6-(10-Undecylenyl)-trehalose | 0 |
| 6-Lauroyl-trehalose | 0 |
| 6-Stearoyl-trehalose | 0 |
| Trehalose-6-soybean fatty acid ester | 0 |
| Trehalose-6-palm fatty acid ester | 0 |
| Control (Monosodium lauryl phosphate) | 0.5 |

As seen from Table 1, the trehalose-6-fatty acid ester of the invention has no irritation to skin and has excellent safety to skin.

EXAMPLES 6–8

Preparation of a Skin Washing Agent

Liquid skin washing agents having the compositions shown in Table 2 were prepared using the 6-(10-undecylenyl)-trehalose, 6-laurolyl-trehalose, trehalose-6-palm oil fatty acid ester prepared above. These washing agents were used to wash face. Soil was removed completely and the feeling was fine.

TABLE 2

| Component | Example 6 wt. % | Example 7 wt. % | Example 8 wt. % |
|---|---|---|---|
| 6-(10-Undecylenyl)-trehalose | 25.0 | — | — |
| 6-Laurolyl-trehalose | — | 15.0 | — |
| Trehalose-6-palm oil fatty acid ester | — | — | 25.0 |
| Miranol C2M (Miranol) | 5.0 | 5.0 | 5.0 |
| Glycerine | 10.0 | 10.0 | 10.0 |
| Carboxyvinyl polymer | 0.6 | 0.6 | 0.6 |
| Perfume (citrus type composition) | 0.4 | 0.4 | 0.4 |
| Water | 59.0 | 69.0 | 59.0 |

EXAMPLES 9 AND 10

Preparation of a Hair Washing Agent

Hair washing agents having the compositions shown in Table 3 were prepared using the 6-(10-undecylenyl)-trehalose or 6-laurolyl-trehalose prepared above. These washing agents were used to wash hair. Foaming was excellent and the feeling was fine.

TABLE 3

| Component | Example 9 wt. % | Example 10 wt. % |
|---|---|---|
| 6-(10-Undecylenyl)-trehalose | 20.0 | — |
| 6-Laurolyl-trehalose | — | 20.0 |
| Palm oil fatty acid diethanol amide | 5.0 | 5.0 |
| Cationated cellulose | 0.5 | 0.5 |
| Perfume (fresh floral composition) | 0.5 | 0.5 |
| Water | 74.0 | 74.0 |

EXAMPLES 11–13

Preparation of Oil-in-water Skin Creams

Oil-in-water skin creams having the compositions shown in Table 4 were prepared using the above-prepared 6-(10-undecylenyl)-trehalose, 6-stearoly-trehalose or trehalose-6-soybean fatty acid ester. These creams showed extremely good emulsification, and had fine adaptation to skin without stickiness.

TABLE 4

| Component | Example 11 wt. % | Example 12 wt. % | Example 13 wt. % |
|---|---|---|---|
| 6-(10-Undecylenyl)-trehalose | 1.5 | — | — |
| 6-Stearoly-trehalose | — | 1.5 | — |
| Trehalose-6-soybean fatty acid ester | — | — | 1.5 |
| Glycerol monostearate | 2.4 | 2.4 | 2.4 |
| Cetylalcohol | 4.0 | 4.0 | 4.0 |
| Solid paraffin | 5.0 | 5.0 | 5.0 |
| Squalane | 10.0 | 10.0 | 15.0 |
| Octyldodecyl myristearate | 5.0 | 5.0 | — |
| Glycerine | 5.0 | 5.0 | 5.0 |
| Perfume (floral composition) | 0.1 | 0.1 | 0.1 |
| Water | 67.0 | 67.0 | 67.0 |

Preparation of Cosmetic Compositions

The evaluation for various properties of the cosmetic compositions was performed in accordance with the following method.

(1) Long-Term Stability Test

Each sample was placed in a thermostat bath at 45° C. for 1-6 months, and then its appearance was evaluated by the naked eye.

(2) Sensory Properties Test

The sensory properties were evaluated as a whole for feeling on application (adaptation to skin) and finishing after application (dampish) by three examiners.

(3) Appearance Testing

The skin surface texture and beauty were evaluated by the naked eye.

(4) Skin Irritating Test

A patch test adhesive plaster which was impregnated with the sample composition was put on 20 subjects for 24 hours, and then irritation was evaluated 24 or 48 hours after the detachment of the adhesive plaster. Individuals who showed clear erythema were regarded as positive. The result is indicated as a ratio of the positives.

EXAMPLES 14–17

Preparation of Skin Milks

Skin milks were prepared with the formulations shown in Table 5 using the above-prepared 6-luroyl-trehalose as the trehalose-6-fatty acid ester in the following manner. Components 1–5 in Table 5 were mixed and dissolved homogeneously at about 80° C. (Solution 1). Components 6–10 and 12 in the Table were mixed and dissolved homogeneously at about 80° C. (Solution 2). The above Solution 2 was then added to Solution 1 under stirring with a homomixer to emulsify them, and then the mixture was cooled to room temperature under stirring. During the cooling, Component 11 was added at a time when the temperature became 70° C., and further the mixture was cooled to room temperature before stopping the stirring.

Properties of the resultant skin milks are as shown in Table 5.

TABLE 5

| Component | Ex. 14 | Ex. 15 | Ex. 16 | Ex. 17 |
|---|---|---|---|---|
| glyceryl monostearate (selfemulsification type) | 1.0 | 1.0 | 1.0 | 1.0 |
| liquid paraffin | 10.0 | 10.0 | 10.0 | 10.0 |
| squalane | 1.0 | 1.0 | 1.0 | 1.0 |
| cholesterol | 0.5 | 0.5 | 0.5 | 0.5 |
| cetylalcohol | 0.1 | 0.1 | 0.1 | 0.1 |
| dipropyleneglycol | 5.0 | 5.0 | 5.0 | 5.0 |
| glycerine | 1.0 | 1.0 | 1.0 | 1.0 |
| carboxyvinyl polymer | 0.3 | 0.3 | 0.3 | 0.3 |
| 6-lauroyl-trehalose | 0.1 | 0.5 | 1.0 | 5.0 |
| methyl para-hydrooxybenzoate | 0.2 | 0.2 | 0.2 | 0.2 |

TABLE 5-continued

| Component | Ex. 14 | Ex. 15 | Ex. 16 | Ex. 17 |
|---|---|---|---|---|
| perfume | 0.2 | 0.2 | 0.2 | 0.2 |
| purified water | balance | balance | balance | balance |
| Properties | | | | |
| long-term stability (45° C., 4 months) | good | good | good | good |
| sensory properties | | | | |
| (adapting to skin) | good | good | good | good |
| (dampish feeling) | good | good | good | good |
| appearance | good | good | good | good |
| irritation to skin (positive, %) | 0 | 0 | 0 | 0 |

As seen from this Table, the skin milks of Examples 14–17 had excellent long-term stability, sensory properties and appearance, and also had no irritation to skin.

COMPARATIVE EXAMPLES 1–3

Preparation of Skin Milks

Skin milks were prepared with the formulations shown in Table 6 as in Examples 14–17.

The properties of the resultant skin milks are as shown in Table 6.

TABLE 6

| Component | Comp. Ex. 1 | Comp. Ex. 2 | Comp. Ex. 3 |
|---|---|---|---|
| glyceryl-monostearate (selfemulsification type) | 1.0 | 1.0 | 1.0 |
| liquid paraffin | 10.0 | 10.0 | 10.0 |
| squalane | 1.0 | 1.0 | 1.0 |
| cholesterol | 0.5 | 0.5 | 0.5 |
| cetylalcohol | 0.1 | 0.1 | 0.1 |
| dipropyleneglycol | 5.0 | 5.0 | 5.0 |
| glycerine | 1.0 | 1.0 | 1.0 |
| carboxyvinyl polymer | 0.3 | — | 0.3 |
| 6-lauroyl-trehalose | — | 1.0 | — |
| sucrose fatty acid ester | — | — | 1.0 |
| methyl para-hydroxybenzoate | 0.2 | 0.2 | 0.2 |
| perfume | 0.2 | 0.2 | 0.2 |
| purified water | balance | balance | balance |
| Properties | | | |
| long-term stability (45° C., 4 months) | separated | separated | good |
| sensory properties | | | |
| (adapting to skin) | bad | bad | good |
| (dampish feeling) | inferior | inferior | good |
| appearance | bad | inferior | good |
| irritation to skin (positive, %) | 0 | 0 | 0.5 |

As seen from this Table, Comparative Example 1 which lacked trehalose-6-fatty acid ester and Comparative Example 2 which lacked a water-soluble polymer had problems in the long-term stability, sensory properties and appearance. On the other hand, Comparative Example 3 which contained sucrose fatty acid ester which is an emulsifier usually used for cosmetics had a problem in the irritation to skin.

EXAMPLES 18–20 AND COMPARATIVE EXAMPLES 4 AND 5

Preparation of Skin Creams

Skin milks were prepared with the formulations shown in Table 7 using the above-prepared 6-stearoyl-trehalose as the trehalose-6-fatty acid ester in the following manner.

Components 1–7 in Table 7 were mixed and dissolved homogeneously at about 80° C. (Solution 1). Components 7–9 and 11 in the Table were mixed and dissolved homogeneously at about 80° C. (Solution 2). The above Solution 2 was then added to Solution 1 under stirring with a homomixer to emulsify them, and subsequently the mixture was cooled to room temperature under stirring. During the cooling, Component 10 was added at a time when the temperature became 70° C., and further the mixture was cooled to room temperature before stopping the stirring.

Properties of the resultant skin creams are as shown in Table 7.

TABLE 7

| Component | Ex. 18 | Ex. 19 | Ex. 20 | Comp. 4 | Comp. 5 |
|---|---|---|---|---|---|
| olive oil | 5.0 | 5.0 | 5.0 | 5.0 | 5.0 |
| liquid paraffin | 15.0 | 15.0 | 15.0 | 15.0 | 15.0 |
| beeswax | 2.0 | 2.0 | 2.0 | 2.0 | 2.0 |
| cetylalcohol | 8.0 | 8.0 | 8.0 | 8.0 | 8.0 |
| glycelyl monostearate | 3.0 | 3.0 | 3.0 | 3.0 | 3.0 |
| white vaseline | 3.0 | 3.0 | 3.0 | 3.0 | 3.0 |
| 6-stearoly-trehalose | 1.0 | 1.0 | 1.0 | 1.0 | — |
| xanthan gum | 0.01 | 0.5 | 1.0 | — | 10.0 |
| methyl para-hydroxybenzoate | 0.3 | 0.3 | 0.3 | 0.3 | 0.3 |
| perfume | 0.1 | 0.1 | 0.1 | 0.1 | 0.1 |
| purified water | balance | balance | balance | balance | balance |
| Properties | | | | | |
| long-term stability (45° C., 6 months) | good | good | good | separated | separated |
| sensory properties | | | | | |
| (adapting to skin) | good | good | good | good | bad |
| (dampish feeling) | good | good | good | good | inferior |
| appearance property | good | good | good | good | bad |
| irritation to skin (positive, %) | 0 | 0 | 0 | 0 | 0 |

As seen from this Table, the skin creams of Examples 18–20 had excellent long-term stability, sensory properties and appearance, and also had no irritation to skin. On the other hand, Comparative Example 5 which lacked trehalose-6-fatty acid ester had problems in long-term stability, sensory properties and appearance. Comparative Example 4 which lacked a water-soluble polymer had a problem in long-term stability.

EXAMPLE 21

Preparation of a Makeup Base

A makeup base was prepared with the following formulation. Trehalose monoisostearate used in this example was synthesized from trehalose and methyl isostearate as in Example 1.

Formulation:

| Component | |
|---|---|
| 1. liquid paraffin | 12.0 |
| 2. squalane | 3.0 |
| 3. glycelol monostearate | 1.5 |
| 4. cholesterol | 0.2 |
| 5. cetylalcohol | 0.5 |

-continued

| Formulation: | |
|---|---|
| Component | |
| 6. trehalose monoisostearate | 1.5 |
| 7. glycerin | 5.0 |
| 8. carageenan | 0.5 |
| 9. methyl para-hydoxybenzoate | 0.3 |
| 10. xthantan gum | 1.0 |
| 11. dipropyleneglycol | 0.8 |
| 12. titanium oxide | 0.5 |
| 13. perfume | 0.1 |
| 14. purified water | balance |

The oil components 1–6 in the above formulation were mixed and dissolved at about 80° C. (Solution 1). The aqueous components 7–10 and 14 were mixed and melted at about 80° C. (Solution 2). Also, Component 12 was dispersed in Component 11 (Dispersion). The above Solution 2 was then added to Solution 1 under stirring with a homomixer to emulsify them. Subsequently, Dispersion 1 was added to the mixture and stirred. The mixture was cooled to room temperature under stirring. During the cooling, Component 13 was added at a time when the temperature become 70° C., and further the mixture was cooled to room temperature before stopping the stirring.

The makeup base thus prepared was an oil-in-water emulsion. After 4-month storage in a thermostat bath at 45° C. it had extremely good stability and also had good sensory properties (adapting to skin, dampish feeling) and good appearance (surface texture).

EXAMPLE 22

Preparation of A Hair Cream

A hair cream was prepared with the following formulation. Trehalose monodocosanate used in this example was synthesized from trehalose and methyl docosanate as in Example 1.

| Formulation: | |
|---|---|
| Component | |
| 1. stearic acid | 0.5 |
| 2. squalane | 2.0 |
| 3. liquid paraffin | 40.0 |
| 4. glycelol monostearate | 0.5 |
| 5. dimethylpolysiloxane | 1.0 |
| 6. butyl para-hydoxybenzoate | 0.1 |
| 7. trehalose monodocosanate | 2.0 |
| 8. propyleneglycol | 2.0 |
| 9. sorbitol | 3.0 |
| 10. glycerin | 3.0 |
| 11. methylcellulose | 0.3 |
| 12. tetra-sodium edetate | 0.1 |
| 13. methyl para-hydoxybenzoate | 0.2 |
| 14. sodium chondroitin sulfate | 0.3 |
| 15. perfume | 0.3 |
| 16. purified water | balance |

The oil components 1–7 in the above formulation were mixed and dissolved at about 80° C. (Solution 1). The aqueous components 8–14 and 16 were mixed and melted at about 80° C. (Solution 2). The above Solution 2 was then added to Solution 1 under stirring with a homomixer to emulsify them, and cooled to room temperature under stirring. During the cooling, Component 15 was added just at a time when the temperature became 70° C., and further the mixture was cooled to room temperature before stopping the stirring.

The hair cream thus obtained had extremely good stability after 6-month storage in a thermoatat bath at 45° C. It had also good sensory properties (adapting to skin, dampish feeling) and good appearance (surface texture).

EXAMPLE 23

Preparation of A Cleansing Cream

A cleansing cream was prepared with the following formulation. The trehalose monolinoleate and the trehalose monocaprateused in this Example were synthesized from trehalose and methyl linolenate or methyl caprate as in Example 1.

| Formulation: | |
|---|---|
| Component | |
| 1. beeswax | 5.0 |
| 2. cetylalcohol | 2.0 |
| 3. liquid paraffin | 15.0 |
| 4. vaseline | 17.0 |
| 5. glycelol monostearate | 3.0 |
| 6. dimethylpolysiloxane | 3.0 |
| 7. butyl para-hydoxybenzoate | 0.1 |
| 8. trehalose monolinoleate | 3.0 |
| 9. trehalose monocaprate | 3.0 |
| 10. sodium N-stearoyl-L-glutamate | 2.0 |
| 11. glycerin | 4.0 |
| 12. methyl para-hydoxybenzoate | 0.3 |
| 13. dipropyleneglycol | 2.0 |
| 14. polyvinylpyrrolidon | 2.0 |
| 15. purified water | balance |

The oil components 1–8 in the above formulation were mixed and dissolved at about 80° C. (Solution 1). The aqueous components 9–15 were mixed and melted at about 80° C. (Solution 2). The above Solution 2 was then added to Solution 1 under stirring with a homomixer to emulsify them, and cooled to room temperature under stirring. After that, the stirring was stopped.

The cleansing cream thus prepared had extremely good stability after 6-month storage in a thermostat bath at 45° C. It had also good sensory properties (adapting to skin, dampish feeling) and good appearance (surface texture).

EXAMPLE 24

Preparation of A Massage Jelly

A massage jelly was prepared with the following formulation.

| Formulation: | |
|---|---|
| Component | |
| 1. squalane | 10.0 |
| 2. olive oil | 4.0 |
| 3. vitamin E acetate | 0.2 |
| 4. liquid paraffin | 8.0 |
| 5. polyoxyethylene cetylether(2 E.O) | 2.0 |
| 6. trehalose monolaurate | 2.0 |
| 7. glycerin | 35.0 |

-continued

| Formulation: | |
|---|---|
| Component | |
| 8. dipropyleneglycol | 20.0 |
| 9. polyvinylalcohol | 18.0 |
| 10. dipotassium glycyrrhizeinate | 0.1 |
| 11. purified water | balance |

The oil components 1–6 in the above formulation were mixed and dissolved at about 80° C. (Solution 1). The aqueous components 7–11 were mixed and melted at about 80° C. (Solution 2). The above Solution 2 was then added to Solution 1 under stirring with a homomixer, and the mixture was cooled to room temperature under stirring. After that, the stirring was stopped.

The massage jelly thus prepared had extremely good stability after 6-month storage in a thermostat bath at 45° C. It had also good sensory properties (adapting to skin, dampish feeling) and good appearance (surface texture).

EXAMPLE 25

Preparation of A Cleansing Gel

The cleansing gel was prepared with the following formulation. Trehalose monomyristate used in this Example was synthesized from trehalose and methyl myristate as in Example 1.

| Formulation: | |
|---|---|
| Component | |
| 1. 2-ethyl hexanoic acid triglyceride | 5.0 |
| 2. olive oil | 41.0 |
| 3. liquid paraffin | 15.0 |
| 4. dimethylpolysiloxan | 2.0 |
| 5. glycerin | 20.0 |
| 6. trehalose monolaurate | 7.0 |
| 7. trehalose monomyristate | 2.0 |
| 8. polyoxyethylenesorbitan monolaurate(20 E.O.) | 2.0 |
| 9. carboxyvinyl polymer | 0.7 |
| 10. purified water | balance |

The oil components 1–4 in the above formulation were mixed and dissolved at about 80° C. (Solution 1). The aqueous components 5–10 were mixed and melted at about 80° C. (Solution 2). The above Solution 2 was then added to Solution 1 under stirring with a homomixer, and the mixture was cooled to room temperature under stirring. After that, the stirring was stopped.

The cleansing gel thus prepared had extremely good stability after 6-month storage in a thermostat bath at 45° C. It had also good sensory properties (adapting to skin, dampish feeling) and good appearance (surface texture).

The present invention relates also to a liposome which is characterized in that it has a wall membrane formed from trehalose fatty acid ester and which is useful in drugs, quasi-drugs cosmetics and so forth.

Liposome is a closed vesicle whose wall membrane is composed of a lipid bilayer. Natural biomembrane is said to have lipid dyad membrane structure. The liposome has biomembrane-like structure. Therefore, it is expected that the liposome has high affinity with biocell membrane and has high potential as a drug carrier. Recently, the development of liposome formulations aiming at a drug delivery system has been desired not only in the fields of pharmaceuticals, but in cosmetics.

Phospholipid (lecithin) has been used as a liposome forming agent. This is excellent in safety, but is hardly used in practical applications because of its poor chemical and physical stabilities. In other words, chemical changes such as changes of color and smell occur in long-term storage in the case where liposome is prepared with phospholipid. Also, physical changes such as aggregation and precipitation occur after long-term storage or by rehydration after freeze-drying. Because of these problems, liposomes from phospholipid have not been put to practical use.

It was tried to find other substance which has liposome-forming activity to solve these problems. For example, there are publications on dialkyl-type cationic surfactants such as dialkyldimethylammonium bromide (Kunitake et al. J. Am. Chem. Soc., vol 99, p3860, 1977), POE-type nonionic surfactants such as polyoxyethylene cured castor oil (Japanese Patent Application Laid Open No. 52-6375/1977, and No. 59-16534/1984). Also, there are reported sucrose fatty acid esters (Japanese Patent Application Laid Open No. 61-207324/1986), glucose fatty acid esters (Japanese Patent Application Laid Open No. 4-300820/1991), and glucose alkylether (Japanese Patent Application Laid Open No. 59-106423/1984), in which sugars are used as a hydrophilic group. However, the stability of these liposomes is not satisfactory.

Also, in order to improve the stability of liposome, sugars such as trehalose are added to liposome (Japanese Patent Application Laid Open No. 62-500102/1987, and No. 62-501631/1987). However, there is no report in which trehalose fatty acid ester is used as a liposome forming agent.

Meanwhile, there are some report on trehalose fatty acid ester, such as a report on its synthesis (Chem. Pharm. Bull., 30(4), pp1169–1174(1982), a report aiming to use trehalose difatty acid ester as a surfactant (Japanese Patent Application Laid Open No. 60-258195/1985 and No. 62-91236/1987), and a report aiming to use it as an antitumor agent (Japanese Patent Application Laid Open No. 61-289038/1986, Chem. Pharm. Bull., vol 25(7), pp1717–1724). However, there is no report which discloses or suggests the liposome forming activity.

A further object of the invention is to provide a liposome which has excellent chemical and physical stabilities such as storage stability.

The prersent invention is a liposome, characterized in that it has membrane wall composed of a trehalose fatty acid ester.

The present invention is a liposome, characterized in that it has membrane wall composed of trehalose difatty acid ester.

The present invention will be explained further in details below.

The trehalose fatty acid ester used in the invention can be obtained from trehalose and a fatty acid or ester thereof in a known synthesis method, such as by ester exchange reaction between trehalose and a lower alkyl ester of a fatty acid.

The trehalose fatty acid ester can be produced, for example, in a method for the preparation of sucrose fatty acid esters disclosed in U.S. Pat. Nos. 2,893,990 and 3,963,699, Japanese Patent Application Laid Open No. 36-21717/1961 and No. 53-6130/1978, all of which are incorporated herein by reference.

Trehalose may be any of α,α-trehalose, α,β-trehalose or β,β-trehalose or mixtures of two or more of them.

In these methods, a mixture of mono-fatty acid ester, di-fatty acid ester and tri- or more fatty acid ester of trehalose are obtained as reaction products. These products can be isolated by any conventional purification methods. However, the mixture of trehalose fatty acid ester can be used without any purification.

As the trehalose fatty acid ester, preferred are trehalose poly-fatty acid esters, particularly diesters. The fatty acid to compose the trehalose fatty acid ester is preferably those having 8–22 carbon atoms, particularly saturated or unsaturated higher fatty acids having 10–18 carbon atoms. Examples of those include trehalose caprylate, trehalose nonanate, trehalose caprate, trehalose undecanate, trehalose laurate, trehalose myristate, trehalose palmitate, trehalose stearate, trehalose arachidonaeate, trehalose docosanate, trehalose undecylenate, trehalose oleate, trehalose linolate, trehalose linolenate, trehalose isostearate, trehalose monohydroxystearate, and trehalose ricinoleate. These fatty acids may be used alone or as a mixture. The diesters are not required to be of high purity, and the content of the diesters is preferably 30 wt. % or more, based on the total weight of the trehalose fatty acid ester.

The liposome of the invention may contain unreacted raw materials, i.e. trehalose and fatty acid esters in such an amount as not to adversely affect the liposome formation.

The liposome of the invention may be composed of a single species of trehalose fatty acid ester or a mixture of two or more species.

The liposome of the invention may contain sterols, such as cholesterol and cholestanol, as a membrane stabilizer; dicetylphosphate, phosphatidic acid, ganglioside, stearylamine and so forth, as a charged substance; and β-tocopherol as an antioxidant. These substances may be added preferably in amounts of about 0.01 to about 2.0 weight parts per weight part of the trehalose fatty acid ester, but not limited to such a range.

Any conventional methods for preparing a liposome can be used in the invention. For example, a vortexing method, a sonication method, a pre-vesicle method, an ethanol injection method, a French press method, an ether injection method, an annealing method, a W/O/W emulsion method, a reverse phase evaporation method and so forth can be mentioned. Any of them or any combination of them can be used, but not limited to these.

Preparation in a vortexing method or sonication method will be explained below.

A trehalose fatty acid ester and a membrane stabilizer and any optional substances are dissolved in an organic solvent, preferably chloroform, and the organic solvent was evaporated out to form a thin membrane composed of the trehalose fatty acid ester. A buffer solution in which a water-soluble component, etc. were dissolved was added, and was vortexed at or above its phase transition temperature to strip off the membrane. At this point of time, a polylayer liposome (MLV) was formed. Then, a single layer liposome (SUV) was obtained by sonication, if desired.

The liposome of the invention may contain ordinary pharmaceutical components such as water-soluble polymers, polyvalent alcohols, preservatives and chelating agents.

EXAMPLES

This invention will be explained further in details in the following Examples, but not limited to those.

EXAMPLE A

One hundred mg of trehalose dilaurate was charged in a 50 ml volume eggplant type flask, and dissolved by adding 5 ml of chloroform. Then, this flask was set on a rotary evaporator, and the solvent was evaporated out slowly so that a thin membrane of trehalose dilaurate was formed on the inner wall of the flask. The inside of the flask was then evacuated by a vacuum pump to be dried for additional 3 hours. Four millilitres of distilled water were added and shaked at 60° C. to strip off the thin membrane. Thus, an aqueous cloudy liquid was obtained. In observation by a polarizing microscope (×400), particles of 1–10 μm in diameter were seen with "closed lamella structure" which is characteristic of MLV. This aqueous liquid was stained with phosphotungstic acid. In observation by a transmission electron microscope (×100,000), closed vesicles having about five- to nine-layer membrane structure, i.e., liposomes, were observed. Then, this aqueous liquid was sonicated by a probe-type sonicator for 10 min. at 60° C. In observation by a transmission electron microscope as above, SUV's of 50–80 nm in particle diameter were observed.

EXAMPLE B

Liposomes were prepared in accordance with the procedures of Example A except that a 100 mM aqueous carboxyfluorescein (CF) solution was substituted for distilled water. After MLV's were formed, a liposome solution was gel filtrated to remove CF present in the exterior phase (i.e., not contained in liposomes). Then, liposomes were destroyed by adding an aqueous Triton X-100 solution. By measuring the fluorescence intensities before and after the addition of the aqueous Triton X-100 solution, it was confirmed that CF was trapped in the interior phase (inside the liposomes). The retaining efficiency was 15.5%.

EXAMPLE C

Liposomes were prepared in accordance with the procedures of Example A except that trehalose dipalmitate was substituted for trehalose dilaurate. In observation by an electron microscope, it was confirmed that MLV's and SUV's were formed.

EXAMPLE D

A mixture of 20 mg of trehalose monomyristate, 60 mg of trehalose distearate and 20 mg of trehalose tri- or more stearate was added to 8 ml of ethanol and dissolved by heating at 50° C. The solution was pressure injected into distilled water heated at 60° C. by a syringe. As a result, an aquous translucent solution was obtained. In observation by an electron microscope as in Example A, it was confirmed that SUV's were formed.

The results of Examples A–D showed that trehalose fatty acid esters could form liposomes.

In the following, the liposome of the invention was compared with the liposome of prior art for stability.

EXAMPLE E

One gram of Trehalose diundecylenate, 0.5 g of cholesterol and 0.2 g of dicetylphosphate were charged in a 200 ml volume eggplant type flask and dissolved by adding 10 ml of chloroform. Then, this flask was set on a rotary evaporator, and the solvent was evaporated out slowly so that a thin membrane was formed on the inner wall of the flask. The inside of the flask was then evacuated by a vacuum pump to be dried for additional 3 hours. One hundred millilitres of distilled water were added and shaked at 60° C. to strip off the thin membrane. Then, this solution was sonicated by a probe-type sonicator for 10 min. at 60° C. to prepare SUV's. In observation by a dynamic light scattering method, the particle diameter was 62 nm.

EXAMPLE F

A mixture of 0.2 g of trehalose monomyristate, 0.6 g of trehalose distearate and 0.2 g of trehalose tri- or more stearate was added to 10 ml of ethanol and dissolved by heating at 50° C. The solution was pressure injected into distilled water heated at 60° C. by a syringe to prepare SUV's. In observation by a dynamic light scattering method, the particle diameter was 73 nm.

COMPARATIVE EXAMPLE A

SUV's were prepared in accordance with the procedures of Example E except that hydrogenated soybean lecithin was substituted for trehalose diundecylenate. In observation by a dynamic light scattering method, the particle diameter was 59 nm.

COMPARATIVE EXAMPLE B

SUV's were prepared in accordance with the procedures of Example E except that sucrose diundecylenate was substituted for trehalose diundecylenate. In observation by a dynamic light scattering method, the particle diameter was 70 nm.

After storing the liposomes which were prepared in Examples E and F and Comparative Examples A and B for 3 months at 40° C., the changes of color, smell and particle diameter were examined. The results are as shown in Table A.

Further, the liposomes were each freeze-dried and re-hydrated, and then their particle diameters were measured. The results are as shown in Table B.

TABLE A

| Conditions after 3 Month-Storage at 40° C. | | |
|---|---|---|
| | color change | foul smell | particle diameter, nm |
| Example E | no | no | 75 |
| Example F | no | no | 80 |
| Comp. Ex. A | yellowish | egg smell | 159 |
| Comp. Ex. B | no | no | 142 |

TABLE B

| Particle Diameter After Freeze-Drying and Re-Hydration | |
|---|---|
| | particle diameter, nm |
| Example E | 72 |
| Example F | 77 |
| Comp. Ex. A | 189 |
| Comp. Ex. B | 112 |

Tables A and B show that the liposomes of the invention showed superior stability compared with the liposomes of the prior art prepared from hydrogenated soybean lechitin or sucrose fatty acid ester.

The results of Examples E and F were better than those of Comparative Example B. The reason of these results is considerably that the molecular structure of trehalose diundecylenate is more symmetrical than that of sucrose diundecylenate, which contributes to the stability of the liposomes.

The liposome of the invention has excellent stability. Also, the liposome of the invention can properly envelop water-soluble or oil-soluble drugs and does not suffer from chemical and physical changes. Therefore, the liposome of the invention is useful in the fields of drugs, quasi-drugs, cosmetics and so forth, and can provide liposome formulations suitable for injection drugs, oral medicines, external medicines, lotions, emulsions, creams, essences, and hair tonics.

What is claimed is:

1. A liposome comprising a membrane wall composed of a trehalose fatty acid ester, wherein the fatty acid of said trehalose fatty acid ester is a saturated or unsaturated fatty acid having 10–18 carbon atoms.

2. The liposome as claimed in claim 1, wherein said trehalose fatty acid ester is trehalose difatty acid ester.

3. The liposome as claimed in claim 1, wherein the fatty acid of which said trehalose fatty acid ester is constituted is a saturated or unsaturated fatty acid which has 10–18 carbon atoms and is unsubstituted or has a hydroxyl group.

4. A liposome comprising a membrane wall substantially comprised of at least one trehalose fatty acid ester selected from the group consisting of trehalose dilaurate, trehalose dipalmitate, trehalose diundecylenate, trehalose dimyristate and trehalose distearate.

* * * * *